United States Patent [19]

Jung et al.

[11] Patent Number: 5,523,444
[45] Date of Patent: Jun. 4, 1996

[54] BIS(SILYLPROPYL)ARENES AND THEIR PREPARATION METHODS

[75] Inventors: Il N. Jung; Sang K. Park; Bong W. Lee; Mi-Yeon Suk, all of Seoul, Rep. of Korea

[73] Assignee: Korea Institute of Science and Technology, Seoul, Rep. of Korea

[21] Appl. No.: 494,264

[22] Filed: Jun. 23, 1995

[30] Foreign Application Priority Data

Jun. 25, 1994 [KR] Rep. of Korea .................. 14748/1994

[51] Int. Cl.$^6$ .................. C07F 7/08; C07F 7/16; C07F 7/10
[52] U.S. Cl. .................. 512/431; 556/415
[58] Field of Search .................. 556/431, 415

[56] References Cited

U.S. PATENT DOCUMENTS

| | | | |
|---|---|---|---|
| 3,304,320 | 2/1967 | Spencer | 556/431 |
| 4,647,682 | 3/1987 | Panster et al. | 556/431 |
| 4,861,901 | 8/1989 | Lau et al. | 556/431 X |
| 4,902,368 | 2/1990 | Oldham | 556/431 X |
| 5,338,876 | 8/1994 | Jung et al. | |
| 5,386,050 | 1/1995 | Jung et al. | |

OTHER PUBLICATIONS

N. S. Nametkin, V. M. Vdovin, E. S. Finkelshtein, V. D. Oppengeium, and N. A. Chekalina. "Alkylation of Aromatic Compounds by Allylsilane Chlorides", 1966.

*Primary Examiner*—Paul F. Shaver
*Attorney, Agent, or Firm*—Oblon, Spivak, McClelland, Maier & Neustadt

[57] ABSTRACT

The present invention relates to bis(silylpropyl)arenes represented by the formula I and their preparation methods by reacting aromatic compounds represented by the formula II or III with allylchlorosilanes represented by the formula IV in the presence of Lewis acid catalysts such as aluminum chloride:

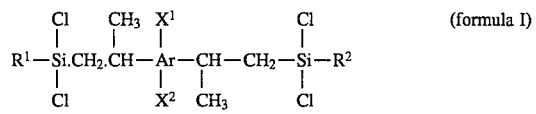

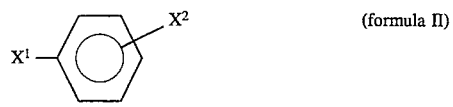

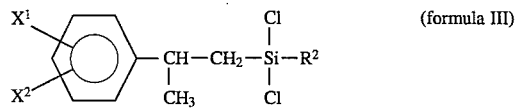

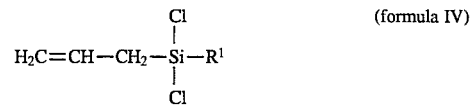

wherein $R^1$ and $R^2$ which may be the same or different represent hydrogen, chloro or $-(CH_2CH_2)-R^3$ (wherein $R^3$ is Ph, $CH_2Cl$, $C_nH_{2n}CH_3$ (n=0–15), $CF_3$, $CH_2CF_3$, $Si(Me)_mCl_{3-m}$(m=0–3), CN, $CH_2CN$, (p—Ph)—$CH_2Cl$ or 3-cyclohexenyl group); Ar represents phenyl ring, phenoxyphenyl ring, or biphenyl ring; $X^1$ represents hydrogen or methyl; and $X^2$ represents hydrogen, alkyl($C_1$–$C_4$), fluoro, chloro, bromo, phenyl or phenoxy group.

13 Claims, No Drawings

BIS(SILYLPROPYL)ARENES AND THEIR PREPARATION METHODS

FIELD OF THE INVENTION

The present invention relates to bis(silypropyl)arenes represented by the formula I and their preparation methods by reacting aromatic compounds represented by the formula II or III with allylchlorosilanes represented by the formula IV in the presence of Lewis acid catalysts such as aluminum chloride;

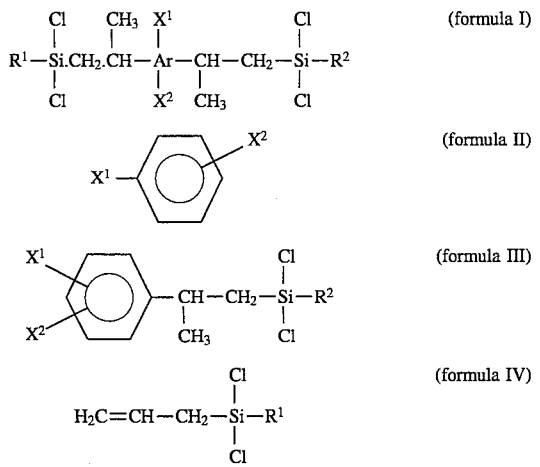

wherein $R^1$ and $R^2$ which may be the same or different represent hydrogen, chloro or —(CH$_2$CH$_2$)—R$^3$ (wherein $R^3$ is Ph, CH$_2$Cl, C$_n$H$_{2n}$CH$_3$ (n=0–15), CF$_3$, CH$_2$CF$_3$, Si(Me)$_m$Cl$_{3-m}$(m=0–3), CN, CH$_2$CN, (p—Ph)—CH$_2$Cl or 3-cyclohexenyl group); Ar represents phenyl ring, phenoxyphenyl ring or biphenyl ring; $X^1$ represents hydrogen or methyl; and $X^2$ represents hydrogen, alkyl(C$_1$–C$_4$), fluoro, chloro, bromo, phenyl or phenoxy group.

DESCRIPTION OF THE PRIOR ART

The present inventors reported a preparation method of allylchlorosilanes by directly reacting silicon metal simultaneously with allyl chloride and hydrogen chloride in the presence of copper catalyst at a temperature from 220° C. to 350° C. Allyldichlorosilane was obtained as the major product indicating one mole of each reactant reacted with the same silicon atom (U.S. Pat. No. 5,338,876 (Aug. 16, 1994)). The present inventors also reported that the Friedel-Crafts type addition of allylchlorosilanes to substituted benzenes in the presence of aluminum chloride catalyst to give 3-phenyl-1-silabutanes. (Korean Patent application No. 92-12996(Jul. 21. 1992 )) In this reaction double alkylated products are produced when sufficient substituted benzenes were not used.

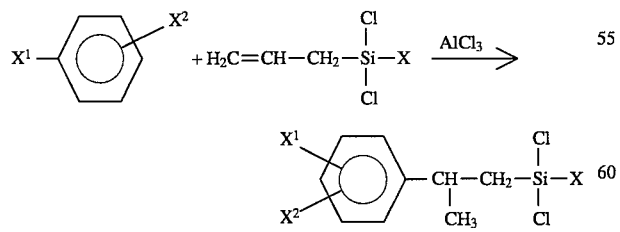

Wherein $X^1$ represents hydrogen or methyl and $X^2$ represents hydrogen, alkyl(C$_1$–C$_4$), fluoro, chloro, bromo, phenyl or phenoxy group and X represents hydrogen or chloro group.

Nametkin and his co-workers reported that the Friedel-Crafts type addition of allylchlorosilanes to mono substituted benzenes to give 3-phenyl-1-silabutanes. (N. S. Nametkin, V. M. Vdovin, E. S. Finkelshtein, V. D. Oppengeium, and N. A. Chekalina, *Izv. Akad. Nauk SSSR, Ser. Khim.*, 1966, 11, 1998) They reacted allyltrichlorosilane, allyldichlorosilane, allymethyldichlorosilane, or allyltrimethylsilane with benzene, chlorobenzene, bromobenzene, or benzyltrichlorosilane in the presence of aluminum chloride to give 2-phenylpropylsilanes. The yield of 1:1 alkylated products was about 60% and the double adducts of bis(silylpropyl)benzenes were also obtained.

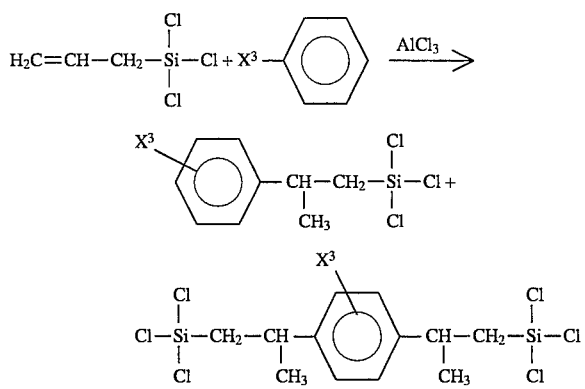

SUMMARY OF THE INVENTION

The present invention relates to bis(silylpropyl)arenes represented by the formula I and their preparation methods by reacting aromatic compounds represented by the formula II or III with allylchlorosilanes represented by the formula IV in the presence of Lewis acid catalysts such as aluminum chloride;

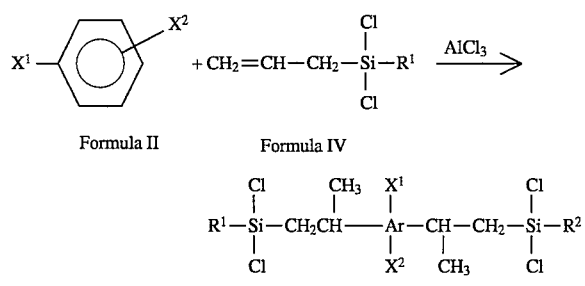

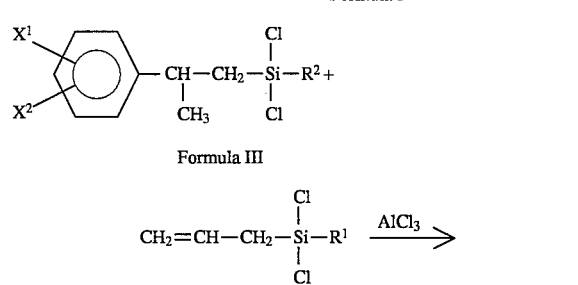

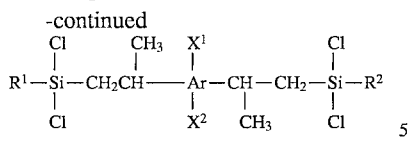

Formula I wherein $R^1$ and $R^2$ which may be the same or different represent hydrogen, chloro or —$(CH_2CH_2)$—$R^3$ (wherein $R^3$ is Ph, $CH_2Cl$, $C_nH_{2n}CH_3$ (n=0–15), $CF_3$, $CH_2CF_3$, Si(Me)$_m$Cl$_{3-m}$(m=0–3), CN, $CH_2CN$, (p—Ph)—$CH_2Cl$ or 3-cyclohexenyl group); Ar represents phenyl ring, phenoxyphenyl ring, or biphenyl ring; $X^1$ represents hydrogen or methyl; and $X^2$ represents hydrogen, alkyl($C_1$–$C_4$), fluoro, chloro, bromo, phenyl or phenoxy group.

DETAILED DESCRIPTION OF THE INVENTION

The bis(silylpropyl)arenes represented by the formula I, produced by the present invention can be classified into two groups. One of them is symmetric bis(silypropyl)arenes wherein $R^1$ and $R^2$ are the same and the other is asymmetric bis(silypropyl)arenes wherein $R^1$ and $R^2$ are different from each other.

The symmetric bis(silylpropyl)arenes are produced by reacting the aromatic compounds represented by formula II with two moles of allylchlorosilanes represented by formula IV in the presence of Lewis acid catalyst such as aluminum chloride.

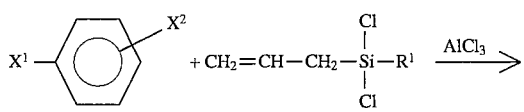

Formula II       Formula IV

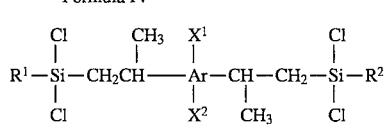

Formula I

In this equation $R^1$ and $R^2$ are same and Ar, $X^1$, and $X^2$ are same as defined above.

The allylchlorosilanes represented by formula IV wherein $R^1$ is hydrogen or chloro are obtained from the direct reaction of silicon metal simultaneously with allyl chloride and hydrogen chloride in the presence of copper catalyst. (U.S. Pat. No. 5,338,876 (Aug. 16, 1994)) The allylchlorosilanes wherein $R^1$ is —$(CH_2CH_2)$—$R^3$ (wherein $R^3$ is Ph, $CH_2Cl$, $C_nH_{2n}CH_3$ (n=0–15), $CF_3$, $CH_2CF_3$, Si(Me)$_m$Cl$_{3-m}$(m=0–3), CN, $CH_2CN$, (p—Ph)—$CH_2Cl$ or 3-cyclohexenyl group) are obtained from the hydrosilylation of allyldichlorosilane with olefins having $R^3$ group in the presence of platinum catalyst. (Korean Patent application No. 93-26069 (Dec. 1, 1993))

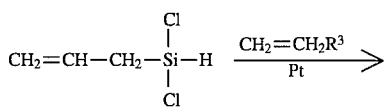

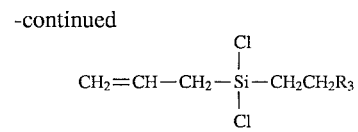

The symmetric bis(silylpropyl)arenes may be also produced by reacting the (2-arylpropyl)chlorosilanes or (2-arylpropyl)alkylchlorosilanes represented by formula III with one mole of allylchlorosilanes represented by formula IV wherein $R^1$ of the compound of formula IV and $R^2$ of the compound of formula III are the same in the presence of Lewis acid catalyst such as aluminum chloride. The (2-arylpropyl)chlorosilanes are obtained from the 1:1 Friedel-Crafts type alkylation of allyldichlorosilane with aromatic compounds in the presence of aluminum chloride catalyst. (Korean Patent application No. 92-12996(Jul. 21, 1992)) The (2-arylpropyl)alkylchlorosilanes are obtained from the hydrosilylation of (2-arylpropyl)chlorosilanes with olefins having $R^3$ group wherein $R^3$ is same as defined above in the presence of platinum catalyst. (U.S. Pat. No. 5,386,050 (Jan. 31, 1995))

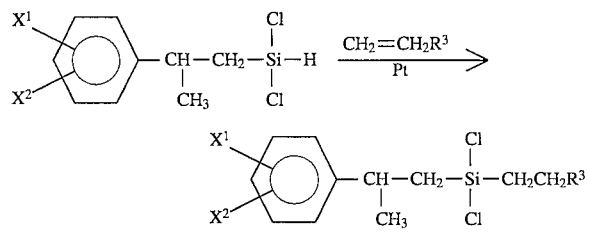

Wherein $X^1$, $X^2$ and $R^3$ are same as defined above.

The asymmetric bis(silylpropyl)arenes may be produced by the following two methods. The first method is the Friedel-Crafts type alkylation reaction of the (2-arylpropyl)chlorosilanes represented by formula III, wherein $R^2$ is hydrogen or chloro group, with one mole of allylchlorosilanes represented by formula IV, wherein $R^1$ is —$(CH_2CH_2)$—$R^3$ (wherein $R^3$ is Ph, $CH_2Cl$, $CH_2CH_3$ (n=0–15), $CF_3$, $CF_2CF_3$, Si(Me)$_m$Cl$_{3-m}$ (m=0–3), CN, $CH_2CN$, (p—Ph)—$CH_2Cl$ or 3-cyclohexenyl group), in the presence of aluminum chloride catalyst. The allylalkyldichlorosilanes are obtained from the hydrosilylation of allyldichlorosilane with olefins having $R^3$ group wherein $R^3$ is the same as defined above in the presence of platinum catalyst (Korean Patent Application No. 93-26069 (Dec. 1, 1993)).

The second method is the Friedel-Crafts type alkylation reaction of the (2-arylpropyl)alkylchlorosilanes represented by formula III, wherein $R^2$ is —$(CH_2CH_2)$—$R^3$ (wherein $R^3$ is Ph, $CH_2Cl$, $C_nH_{2n}CH_3$ (n=0–15), $CF_3$, $CH_2CF_3$, Si(Me)$_m$Cl$_{3-m}$ (m=0–3), CN, $CH_2CN$, (p—Ph)—$CH_2Cl$ or 3-cyclohexenyl group) with one mole of allylchlorosilanes represented by formula IV, wherein $R^1$ is hydrogen or chloro group, in the presence of aluminum chloride catalyst. Allyldichlorosilane are obtained as the major product from the directly reaction of silicon metal with a mixture of allylchloride and hydrogen chloride in the presence of copper catalyst at a temperature from 220° C. to 350° C. (U.S. Pat. No. 5,338,876 (Aug. 16, 1994)).

The preparation of bissilylarenes according to the present invention can be run in standard laboratory glasswares or commercial equipments, under inert atmosphere, with units for external heating and cooling, stirring, and for incremental addition of the start silanes or olefins. The reaction can be carried out in most of nonaromatic or nonprotic solvents, but it also proceeds in neat condition when the aromatic compounds are not solid. In a typical preparation, the aromatic compounds represented by formula II or III and aluminum chloride catalyst are placed in the reactor under inert atmospnere. Aluminum chloride is the best catalyst and can be used alone or in conjunction with other Lewis acid such as chlorides of zinc, boron, titanium, iron, tin, cadmium, and antimony. The allylchlorosilane compounds are then slowly added to the solution with stirring at the reaction temperature between 0° C. and 30° C. Since the alkylation reactions are exothermic, external cooling may be necessary to maintain the reaction temperature. After completion of addition, the solution may be kept stirring for a certain period of time to complete the alkylation and then the products may be fractionally distilled at atmosphere or under vacuum.

The invention will be further illustrated by the following examples. It is, however, not intended that this invention will be limited by the examples.

EXAMPLE 1

Preparation of bis[(2'-dichlorosilyl)isopropyl]benzene

To a 100 ml, three-necked, round bottomed flask equipped with a mechanical stirrer, a dropping funnel, and a reflux condenser, 2.2 g (30 mmol) of benzene and 0.8 g (7.0 mmol) of aluminum chloride as the catalyst were placed under the dry nitrogen atmosphere. The flask was then immersed in an ice water bath. To the reaction mixture was slowly added dropwise 10.0 g (70 mmol) of allyldichlorosilane and the solution was stirred for an hour. Gas chromatographic analysis showed that no benzene was left. 2.0 g (34 mmol) of sodium chloride was added to reaction mixture, warmed up to 70° C. and stirred for another an hour to deactivate the catalyst. Vacuum distillation of the solution gave 4.6 g (bp 121°–124° C./0.5 mmHg) of bis[(2'-dichlorosilyl)isopropyl] benzene in 40% yield.

EXAMPLE 2

Preparation of bis[(2'-dichlorosilyl)isopropyl]toluene

In the same apparatus and procedures as EXAMPLE 1, 6.5 g (71 mmol) of toluene and 0.8 g (7.0 mmol) of aluminum chloride were placed and reacted with 20.0 g (142 mmol) of allyldichlorosilane under the dry nitrogen atmosphere for 40 min. After stirring the solution for another 30 min, 4.0 g (68 mmol) of sodium chloride was added to reaction mixture, warmed up to 70° C. and stirred for another an hour to deactivate the catalyst. Vacuum distillation of the reaction products gave 16.7 g (bp 132°–134° C. /0.5 mmHg) of bis[(2'-dichlorosilyl)isopropyl]toluene 63% yield.

EXAMPLE 3

Preparation of bis[(2'-dichlorosilyl)isopropyl]ethylbenzene

In the same apparatus and procedures as EXAMPLE 1, 3.0 g (28 mmol) of ethylbenzene and 0.4 g (3.5 mmol) of aluminum chloride were placed and reacted with 10.0 g (70 mmol) of allyldichlorosilane under the dry nitrogen atmosphere for 40 min. After confirming that no ethylbenzene was left by gas chromatography, 2.0 g (34 mmol) of sodium chloride was added to reaction mixture, warmed up to 50° C. and stirred for two hours to deactivate the catalyst. Vacuum distillation of the reaction products gave 4.6 g (bp 116°–118° C./0.5 mmHg) of bis[(2'-dichlorosilyl)isopropyl]ethylbenzene in 42% yield.

EXAMPLE 4

Preparation of bis[(2'-dichlorosilyl)isopropyl]isopropylbenzene

In the same apparatus and procedures as EXAMPLE 1, 6.8 g (56 mmol) of isopropylbenzene and 0.8 g (7.0 mmol) of anhydrous aluminum chloride were placed and reacted with 20.0 g (142 mmol) of allyldichlorosilane under the dry nitrogen atmosphere for 50 min. After stirring the solution for another 70 min. 4.0 g (68 mmol) of sodium chloride was added to reaction mixture, warmed up to 50° C. and stirred for another two hours to deactivate the catalyst. Vacuum distillation of the reaction products gave 8.6 g (bp 114°–116° C./0.5mmHg) of bis[(2'-dichlorosilyl)isopropyl]isopropylbenzene in 38% yield.

EXAMPLE 5

Preparation of bis[(2'-dichlorosilyl)isopropyl]-p-xylene

In the same apparatus and procedures as EXAMPLE 1, 7.5 g (71 mmole) of p-xylene and 0.8 g (7.0 mmol) of aluminum chloride were placed and reacted with 20.0 g (142 mmol) of allyldichlorosilane under the dry nitrogen atmosphere for 40 min. After stirring the solution for another 30 min, 4.0 g (68 mmol) of sodium chloride was added to reaction mixture, warmed up to 50° C. and stirred for another two hours to deactivate the catalyst. Vacuum distillation of the reaction products gave 17.4 g (bp 134°–136° C./0.5 mmHg) of bis[(2'-dichlorosilyl)isopropyl]-p-xylene in 63% yield.

EXAMPLE 6

Preparation of bis[(2'-dichlorosilyl)isopropyl]ethylbenzene

In the same apparatus and procedures as EXAMPLE 1, 27 g (255 mmol) of ethylbenzene and 1.1 g (9.0 mmol) of aluminum chloride were placed. The flask was then immersed in an ice water bath. To the reaction mixture was slowly added dropwise 12.0 g (85 mmol) of allyldichlorosilane and the solution was stirred for an hour. After confirming that no ethylbenzene was left by gas chromatography, 2.4 g, (413 mmol) of sodium chloride was added to reaction mixture, warmed up to 50° C. and stirred for two hours to deactivate the catalyst. Vacuum distillation of the reaction products gave 16.3 g (bp 80°–84° C./0.6 mmHg) of 3-(ethylphenyl)-1,1-dichloro-1-silabutane.

The mono-alkylated product of 3-(ethylphenyl)-1,1-dichloro- 1-silabutane (16.3 g, 32 mmol) was alkylated again with 4.5 g (32 mmol) of allyldichlorosilane in the presence of 0.18 g (21.6 mmol) of aluminum chloride using the same procedure as described above. Vacuum distillation gave 6.9 g (bp 116°–118° C./0.5 mmHg) of [(2'-dichlorosilyl)-isopropyl]ethylbenzene in 56% yield.

The structures and NMR data of the compounds prepared using the same procedure as described above examples are listed in Table I.

TABLE I $$\text{H—Si(Cl)(CH}_3\text{)—CH}_2\text{.CH(CH}_3\text{)—Ar(X}^1\text{)(X}^2\text{)—CH(CH}_3\text{)—CH}_2\text{—Si(Cl)(Cl)—H}$$

| Substituents | | | NMR data (ppm) | | | | | |
|---|---|---|---|---|---|---|---|---|
| Ar | $X^1$ | $X^2$ | $CH_3(d)$ | CH(hex.) | $CH_2(m)$ | Si—H(br s) | aryl-H(m) | Others ($X^1$ and $X^2$) |
| Ph | H | H | 1.41(1.42) | 3.55 | 1.68–1.73 | 5.46 | 7.22–7.37 | |
| Ph | H | $CH_3$ | 1.47 | 3.23(3.51) | 1.68–1.73 | 5.39(5.47) | 7.00–7.27 | 2.44(2.42), (s, 3H, $CH_3$) |
| Ph | H | $CH_2CH_3$ | 1.47(1.48) | 3.50(3.51) | 1.68–1.72 | 5.38(5.46) | 7.05–7.27 | 1.23(t, 3H, $CH_3$), 2.78(q, 2H, $CH_2$) |
| Ph | H | $CH(CH_3)_2$ | 1.47(1.49) | 3.52(3.53) | 1.67–1.72 | 5.36 | 7.06–7.29 | 1.26(d, 6H, $CH_3$), 2.99(hep, 1H, CH) |
| Ph | H | F | 1.45(1.49) | 3.25(3.83) | 1.65–1.67 | 5.35(5.43) | 6.97–7.27 | |
| Ph | H | Cl | 1.44(1.47) | 3.45(3.99) | 1.56–1.62 | 5.46(5.51) | 7.15–7.37 | |
| Ph | H | Br | 1.43(1.47) | 3.23(3.65) | 1.69–1.78 | 5.46(5.52) | 7.06–7.57 | |
| Ph | H | $CH_3$ | 1.36(1.38) | 3.38 | 1.55–1.71 | 5.36(5.43) | 7.00–7.03 | 2.34(s, 6H, $CH_3$) |
| Ph | $CH_3$ | $CH_3$ | 1.41(1.42) | 3.37(3.66) | 1.11–1.24 | 5.47(5.51) | 6.95–7.27 | 2.35(s, 6H, $CH_3$) |
| Ph-Ph | H | H | 1.46(1.48) | 3.26(3.29) | 1.67–1.74 | 5.47(5.52) | 7.15–7.59 | |
| Ph-O-Ph | H | H | 1.49(1.51) | 3.58(3.72) | 1.61–1.83 | 5.43(5.53) | 6.85–7.34 | |

EXAMPLE 7

Preparation of bis[(2'-trichlorosilyl)isopropyl]benzene

In the same apparatus and procedures as EXAMPLE 1, 1.1 g (14 mmol) of benzene and 0.16 g (1.4 mmol) of aluminum chloride as the catalyst were placed and reacted with 5.0 g (29 mmol) of allyltrichlorosilane under the dry, nitrogen atmosphere for 20 min. After stirring the solution for another an hour. 1.0 g (17 mmol) of sodium chloride was added to reaction mixture, warmed up to 50° C. and stirred for another two hours to deactivate the catalyst. Vacuum distillation of the solution gave 4.0 g (bp 107°–110° C./0.5 mmHg) of bis[(2'-trichlorosilyl)isopropyl]benzene in 65% yield.

EXAMPLE 8

Preparation of bis[(2'-trichlorosilyl)isopropyl]toluene

In the same apparatus and procedures as EXAMPLE 1, 1.1 g (12 mmol) of toluene and 0.16 g (1.4 mmol) of aluminum chloride were placed and reacted with 5.0 g (29 mmol) of allyltrichlorosilane under the dry nitrogen atmosphere for 20 min. After stirring the solution for another 30 min. 1.0 g (17 mmol) of sodium chloride was added to reaction mixture, warmed up to 50° C. and stirred for another an hour to deactivate the catalyst. Vacuum distillation of the reaction products gave 3.6 g (bp 128°–130° C./0.5 mmHg) of bis[(2'-trichlorosilyl)isopropyl]toluene in 67% yield.

EXAMPLE 9

Preparation of bis[(2'-trichlorosilyl)isopropyl]-p-xylene

In the same apparatus and procedures as EXAMPLE 1, 1.8 g (16 mmol) of p-xylene and 0.29 g (2.6 mmol) of aluminum chloride were placed and reacted with 7.0 g (40 mmol) of allyltrichlorosilane for 20 min and the solution was stirred for an hour. After confirming that no p-xylene was left by gas chromatography, 2.0 g (30 mmol) of sodium chloride was added to reaction mixture, warmed up to 50° C. and stirred for two hours to deactivate the catalyst. Vacuum distillation of the reaction products gave 5.7 g (bp 138°–142° C./0.5 mmHg) of bis[(2'-trichlorosilyl)isopropyl]-p-xylene in 78% yield.

EXAMPLE 10

Preparation of bis[(2'-trichlorosilyl)isopropyl]toluene

In the same apparatus and procedures as EXAMPLE 1, 9.7 g (105 mmol) of toluene and 0.2 g (1.5 mmol) of aluminum chloride were placed. The flask was then immersed in an ice water bath. To the reaction mixture was slowly added dropwise 3.0 g (15 mmol) of allyltrichlorosilane and the solution was stirred for an hour. After confirming that no toluene was left by gas chromatography, 0.48 g (8.0 mmol) of sodium chloride was added to reaction mixture, warmed up to 50° C. and stirred for two hours to deactivate the catalyst. Vacuum distillation of the reaction products gave 16.3 g (bp 74°–76° C./0.6 mmHg) of 3-(methylphenyl)-1,1,1-trichloro-1-silabutane in 71% yield.

The mono-alkylated product of 3-(methylphenyl)-1,1-dichloro-1-silabutane (3.2 g, 11.4 mmol) was again alkylated with 2.0 g (1 1.4 mmol) of allyltrichlorosilane in the presence of 0.06 g (0.5 mmol) of aluminum chloride using the same procedure as described above. Vacuum distillation gave 3.8 g (bp 116°–118° C./0.5 mmHg) of bis[(2'-trichlorosilyl)isopropyl]toluene in 72% yield.

The structures and NMR data of the compounds prepared using the same procedure as described above examples are listed in Table II.

TABLE II $$\text{Cl—Si(Cl)(CH}_3\text{)—CH}_2\text{—CH(CH}_3\text{)—Ar(X}^1\text{)(X}^2\text{)—CH(CH}_3\text{)—CH}_2\text{—Si(Cl)(Cl)—Cl}$$

| Substituents | | | NMR data (ppm) | | | | |
|---|---|---|---|---|---|---|---|
| Ar | $X^1$ | $X^2$ | $CH_3$(d) | CH(hex.) | $CH_2$(m) | aryl-H(m) | Others ($X^1$ and $X^2$) |
| Ph | H | H | 1.42(1.41) | 3.20 | 1.78–1.89 | 7.11–7.29 | |
| Ph | H | $CH_3$ | 1.38(1.37) | 3.45(3.16) | 1.75–1.82 | 7.00–7.29 | 2.35(s, 3H, $CH_3$) |
| Ph | H | $CH_2CH_3$ | 1.33 | 3.39 | 1.69–1.78 | 7.03–7.25 | 1.25(t, 3H, $CH_3$), 2.67(q, 2H, $CH_2$) |
| Ph | H | $CH(CH_3)_2$ | 1.31 | 3.40 | 1.64–1.74 | 7.05–7.26 | 1.23(d, 6H, $CH_3$), 2.83(hep, 1H, CH) |
| Ph | H | F | 1.34 | 3.74 | 1.76–1.85 | 7.01–7.33 | |
| Ph | H | Cl | 1.33 | 3.83 | 1.73–1.78 | 7.10–7.31 | |
| Ph | H | Br | 1.32 | 3.72 | 1.75–1.82 | 6.96–7.20 | |
| Ph | H | $CH_3$ | 1.37 | 3.41 | 1.72–1.87 | 6.04–7.20 | 2.33(s, 6H, $CH_3$) |
| Ph | $CH_3$ | $CH_3$ | 1.41 | 3.75 | 1.23–1.35 | 6.84–7.25 | 2.34(s, 6H, $CH_3$) |
| Ph-Ph | H | H | 1.36 | 3.53 | 1.73–1.87 | 7.21–7.52 | |
| Ph-O-Ph | H | H | 1.31 | 3.83 | 1.70–1.86 | 6.91–7.32 | |

EXAMPLE 11

Preparation of bis[(2'-hexyldichlorosilyl)isopropyl]benzene

In the stone apparatus and procedures as EXAMPLE 1, 1.0 g (11 mmol) of benzene and 0.13 g (1.0 mmol) of aluminum chloride as the catalyst were placed and reacted with 5.4 g (22 mmol) of 4,4-dichloro-4-sila-1-decene under the dry nitrogen atmosphere for 20 min. After stirring the solution for another an hour, 1.0 g (17 mmol) of sodium chloride was added to reaction mixture, warmed up to 50° C. and stirred for another two hours to deactivate the catalyst. Vacuum distillation of the solution gave 3.3 g (bp 175°–182° C./0.3 mmHg) of bis[(2'-hexyldichlorosilyl)isopropyl]benzene in 57% yield.

EXAMPLE 12

Preparation of bis[(2'-hexyldichlorosilyl)isopropyl]toluene

In the same apparatus and procedures as EXAMPLE 1, 1.0 g (11 mmol) of toluene and 0.12 g (1.0 mmol) of aluminum chloride were placed and reacted with 5.4 g (22 mmol) of 4,4-dichloro-4-sila-1-decene at room temperature under the dry nitrogen atmosphere for 10 min. After stirring the solution for another an hour, 2.0 g (30 mmol) of sodium chloride was added to a reaction mixture, warmed up to 50° C. and stirred for two hours to deactivate the catalyst. Vacuum distillation of the reaction products gave 3.5 g (bp 180°–188° C./0.5 mmHg) of bis[(2'-hexyldichlorosilyl)isopropyl]toluene in 61% yield.

EXAMPLE 13

Preparation of bis[(2'-hexyldichlorosilyl)isopropyl]-p-xylene

In the same apparatus and procedures as EXAMPLE 1, 1.0 g (9.0 mmol) of p-xylene and 0.12 g (1.0 mmol) of aluminum chloride were placed and reacted with 4.7 g (19 mmol) of 4,4-dichloro-4-sila-1-decene under the dry nitrogen atmosphere for 20 min. After stirring the solution for another 40 min, 2.0 g (30 mmol) of sodium chloride was added to reaction mixture, waged up to 50° C. and stirred for two hours to deactivate the catalyst. Vacuum distillation of the reaction products gave 3.4 g (bp 192°–195° C./0.5 mmHg) of bis[(2'-hexyldichlorosilyl)isopropyl]-p-xylene in 64% yield. The structures and NMR data of the compounds prepared using the same procedure as described above examples are listed in Table III.

TABLE III $$R^1\text{—Si(Cl)(CH}_3\text{)—CH}_2\text{.CH(CH}_3\text{)—Ar(X}^1\text{)(X}^2\text{)—CH(CH}_3\text{)—CH}_2\text{—Si(Cl)(Cl)—R}^1$$

| Substituents | | | | NMR data (ppm) | | | | |
|---|---|---|---|---|---|---|---|---|
| Ar | $R^1$ | $X^1$ | $X^2$ | $CH_3$(d) | CH(hex.) | $CH_2$(m) | aryl-H(m) | Others ($X^1$ and $X^2$; $R^1$) |
| Ph | $(CH_2)_3Cl$ | H | H | 1.43 | 3.19 | 1.59–1.67 | 7.20–7.38 | 0.68–0.89, 1.69–1.80(m, 2H, $CH_2$) |
| Ph | $(CH_2)_3Cl$ | H | $CH_3$ | 1.42 | 3.14 | 1.57–1.63 | 7.05–7.25 | 2.38(s, 3H, $CH_3$), 0.70–0.95, 1.70–1.82(m, 12H, $CH_2$) |
| Ph | $(CH_2)_3Cl$ | H | $CH_2CH_3$ | 1.41 | 3.14 | 1.56–1.61 | 7.05–7.25 | 1.26(t, 3H, $CH_3$), 3.38(q, 2H, $CH_3$), 0.72–0.81, 1.71–1.79(m, 12H, $CH_2$) |
| Ph | $(CH_2)_3Cl$ | $CH_3$ | $CH_3$ | 1.42 | 3.15 | 1.56–1.61 | 7.06–7.25 | 2.35, 2.37(s, 6H, $CH_3$), 3.37(t, 2H, $CH_2$), 0.58–0.74, 1.71–1.82(m, 12H, $CH_2$) |
| Ph | $(CH_2)_2SiMe_2Cl$ | H | H | 1.39 | 3.18 | 1.45–1.59 | 7.08–7.36 | 0.40(s, 12H, $CH_3$), 0.76–1.20(m, 8H, $CH_2$) |
| Ph | $(CH_2)_2SiMe_2Cl$ | H | $CH_3$ | 1.40 | 3.15 | 1.48–1.60 | 7.05–7.35 | 2.36(s, 3H, $CH_3$), 0.41(s, 12H, $CH_3$), 0.75–1.20(m, 8H, $CH_2$) |
| Ph | $(CH_2)_2SiMe_2Cl$ | H | $CH_2CH_3$ | 1.41 | 3.15 | 1.54–1.63 | 7.07–7.29 | 1.26(t, 3H, $CH_3$), 2.82(q, 2H, $CH_2$), 0.78, 1.26(s, 12H, |

TABLE III-continued $$R^1-\underset{\underset{Cl}{|}}{\overset{\overset{Cl}{|}}{Si}}-CH_2.\underset{\underset{}{}}{\overset{\overset{CH_3}{|}}{CH}}-\underset{\underset{X^2\ CH_3}{|\ |}}{\overset{\overset{X^1}{|}}{Ar}}-\overset{}{CH}-CH_2-\underset{\underset{Cl}{|}}{\overset{\overset{Cl}{|}}{Si}}-R^1$$

| Substituents | | | | NMR data (ppm) | | | | |
|---|---|---|---|---|---|---|---|---|
| Ar | R¹ | X¹ | X² | CH₃(d) | CH(hex.) | CH₂(m) | aryl-H(m) | Others (X¹ and X²; R¹) |
| Ph | (CH₂)₂SiMe₂Cl | CH₃ | CH₃ | 1.40 | 3.16 | 1.50–1.61 | 7.06–7.25 | CH₃), 1.07–1.22(m, 8H, CH₂) 2.33, 2.35(s, 6H, CH₃), 0.40(s, 12H, CH₃), 0.75–1.17 (m, 8H, CH₂) |
| Ph | (CH₂)₅CH₃ | H | H | 1.31 | 3.43 | 1.46 | 7.11–7.28 | 1.10–1.33(m, 20H, CH₂), 0.85(t, 6H, CH₃) |
| Ph | (CH₂)₅CH₃ | H | CH₃ | 1.36 | 3.39 | 1.46–1.54 | 6.89–7.18 | 2.35, 2.33(s, 3H, CH₃), 1.11–1.32(m, 20H, CH₂), 0.88 (t, 6H, CH₃) |
| Ph | (CH₂)₅CH₃ | H | CH₂CH₃ | 1.37 | 3.38 | 1.46–1.53 | 6.94–7.18 | 1.14(t, 3H, CH₃), 2.69(q, 2H, CH₂), 1.12–1.32(m, 20H, CH₂), 0.87(t, 6H, CH₃) |
| Ph | (CH₂)₅CH₃ | CH₃ | CH₃ | 1.29 | 3.27 | 1.33–1.52 | 6.93–7.15 | 2.25(s, 6H, CH₃), 1.11–1.32(m, 20H, CH₂), 0.85(t, 6H, CH₃) |

EXAMPLE 14

Preparation of [(2'-dichlorosilyl)isopropyl][(2'-trichlorosilyl)isopropyl]toluene In the same apparatus and procedures as EXAMPLE 1, 19.3 g (210 mmol) of toluene and 0.9 g (7.0 mmol) of aluminum chloride were placed and reacted with 10.0 g (70 mmol) of allyldichlorosilane under the dry nitrogen atmosphere for 30 min. After stirring the solution for another an hour, 2.0 g (30 mmol) of sodium chloride was added to reaction mixture, warmed up to 50° C. and stirred for two hours to deactivate the catalyst. Vacuum distillation of the reaction products gave 11.7 g (bp, 73°–76° C./0.5 mmHg) of of 3-(methylphenyl)-1,1-dichloro-1-silabutane in 71% yield.

The mono-alkylated product of 3-(methylphenyl)-1,1-dichloro-1-silabutane (11.7 g, 51 mmol) was again alkylated with 8.0 g (51 mmol) of allyltrichlorosilane in the presence of 0.28g (2.5 mmol) of aluminum chloride using the same procedure as as described above. Vacuum distillation gave 12.7 g (bp 135°–137° C./0.5 mmHg) of [(2'-dichlorosilyl)isopropyl][(2'-trichlorosilyl)isopropyl]toluene in 62% yield.

EXAMPLE 15

Preparation of [(2'-dichlorosilyl)isopropyl][(2'-hexyldichlorosilyl)-isopropyl]toluene In the same apparatus and procedures as EXAMPLE 1, 19.3 g (210 mmol) of toluene and 0.9 g (7.0 mmol) of aluminum chloride were placed and reacted with 10.0 g (70 mmol) of allyldichlorosilane under the dry nitrogen atmosphere for 30 min. After stirring the solution for another an hour, 2.0 g (30 mmol) of sodium chloride was added to reaction mixture, warmed up to 50° C. and stirred for two hours to deactivate the catalyst. Vacuum distillation of the reaction products gave 11.7 g (bp 73°–76° C./0.5 mmHg) of of 3-(methylphenyl)-1,1-dichloro-1-silabutane in 71% yield.

The mono-alkylated product of 3-(methylphenyl)-1,1-dichloro-1-silabutane (11.7 g, 50 mmol) was again alkylated with 12.5 g (50 mmol) of 4,4-dichloro-4-sila-1-decene in the presence of 0.28g (2.5 mmol) of aluminum chloride using the same procedure as described above. Vacuum distillation gave 12.6 g (bp 163°–167° C./0.6 mmHg) of [(2'-dichlorosilyl)isopropyl][(2'-hexyldichlorosilyl)isopropyl]toluene in 55% yield.

EXAMPLE 16

Preparation of [(2'-trichlorosilyl)isopropyl][(2'-hexyldichlorosilyl)-isopropyl]toluene In the same apparatus and procedures as EXAMPLE 1, 14.6 g (159 mmol) of toluene and 0.18 g (1.6 mmol) of aluminum chloride were placed and reacted with 5.0 g (32 mmol) of allyldichlorosilane under the dry nitrogen atmosphere for 20 min. After stirring the solution for another an hour, 2.0 g (30 mmol) of sodium chloride was added to reaction mixture, warmed up to 50° C. and stirred for two hours to deactivate the catalyst. Vacuum distillation of the reaction products gave 6.3 g (bp 73°–76° C./0.5 mmHg) of of 3-(methylphenyl)-1,1,1-trichloro-1-silabutane in 73% yield.

The mono-alkylated product of 3-(methylphenyl)-1,1,1-trichloro-1-silabutane (6.3 g, 24 mmol) was again alkylated with 5.9 g (24 mmol) of 4,4-dichloro-4-sila-1-decene in the presence of 0.14 g (1.2 mmol) of aluminum chloride using the same procedure as described above. Vacuum distillation gave 6.6 g (bp 164°–167° C./0.6 mmHg) of [(2'-trichlorosilyl)isopropyl][(2'-hexyldichlorosilyl)isopropyl]toluene in 56% yield.

The structures and NMR data of the compounds prepared using the same procedure as described in EXAMPLE 11 and 12 are listed in Table IV.

TABLE IV

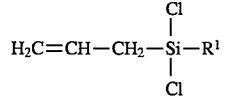

| Substituents | | | | | NMR data (ppm) | | | | |
|---|---|---|---|---|---|---|---|---|---|
| Ar | $R^1$ | $R^2$ | $X^1$ | $X^2$ | $CH_3$(d) | CH(hex.) | $CH_2$(m) | aryl-H(m) | Others ($X^1$ and $X^2$; $R^1$ and $R^2$) |
| Ph | H | Cl | H | H | 1.45 | 3.21 | 1.61–1.69 | 7.21–7.35 | 5.45(br s, 1H, Si—H) |
| Ph | H | Cl | H | $CH_3$ | 1.50 | 3.27 | 1.82–1.95 | 6.96–7.26 | 2.43(s, 3H, $CH_3$), 5.43(br s, 1H, Si—H) |
| Ph | H | Cl | H | $CH_2CH_3$ | 1.45 | 3.21 | 1.76–1.91 | 7.04–7.23 | 1.27(t, 3H, $CH_3$), 2.66(q, 2H, $CH_3$), 5.42(br s, 1H, Si—H) |
| Ph | H | Cl | $CH_3$ | $CH_3$ | 1.49 | 3.26 | 1.74–1.89 | 6.95–7.10 | 2.29, 2.33(s, 6H, $CH_3$), 5.35(br s, 1H, Si—H) |
| Ph | H | $(CH_2)_5CH_3$ | H | H | 1.34 | 3.11 | 1.52–1.59 | 7.18–7.32 | 1.11–1.32(m, 20H, $CH_2$), 0.85(t, 6H, CH3), 5.43(br s, 1H, Si—H) |
| Ph | H | $(CH_2)_5CH_3$ | H | $CH_3$ | 1.40 | 3.14 | 1.60–1.64 | 6.96–7.26 | 2.37(s, 3H, $CH_3$), 1.10–1.32(m, 20H, $CH_2$), 0.88(t, 6H, $CH_3$), 5.34(br s, 1H, Si—H) |
| Ph | H | $(CH_2)_5CH_3$ | H | $CH_2CH_3$ | 1.42 | 3.16 | 1.61–1.65 | 7.05–7.28 | 1.26(t, 3H, $CH_3$), 2.66, (q, 2H, $CH_2$), 1.21–1.31(m, 20H, $CH_2$), 0.87(t, 6H, $CH_3$), 5.33 (br s, 1H, Si—H) |
| Ph | H | $(CH_2)_5CH_3$ | $CH_3$ | $CH_3$ | 1.36 | 3.42 | 1.58–1.66 | 7.00–7.17 | 2.32, 2.36(s, 6H, $CH_3$), 1.11–1.32(m, 20H, $CH_2$), 0.85 (t, 6H, $CH_3$), 5.34(br s, 1H, Si—H) |
| Ph | Cl | $(CH_2)_5CH_3$ | H | H | 1.42 | 3.22 | 1.72–1.88 | 7.16–7.17 | 1.11–1.34(m, 20H, $CH_2$), 0.86(t, 6H, $CH_3$) |
| Ph | Cl | $(CH_2)_5CH_3$ | H | $CH_3$ | 1.48 | 3.25 | 1.80–1.93 | 6.94–7.20 | 2.41(s, 3H, $CH_3$), 1.11–1.33(m, 20H, $CH_2$), 0.88(t, 6H, $CH_3$) |
| Ph | Cl | $(CH_2)_5CH_3$ | H | $CH_2CH_3$ | 1.43 | 3.19 | 1.74–1.89 | 7.02–7.21 | 1.25(t, 3H, $CH_3$), 2.64(q, 2H, $CH_2$), 1.13–1.33(m, 20H, $CH_2$), 0.86(t, 6H, $CH_3$) |
| Ph | Cl | $(CH_2)_5CH_3$ | $CH_3$ | $CH_3$ | 1.47 | 3.24 | 1.72–1.87 | 6.93–7.08 | 2.27, 2.31(s, 6H, $CH_3$), 1.12–1.33(m, 20H, $CH_2$), 0.85 (t, 6H, $CH_3$) |

What is claimed is:

1. Bis(silylpropyl)arenes represented by the formula I:

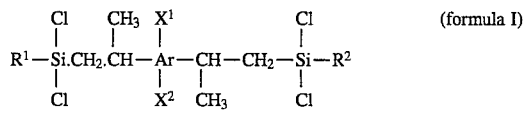
(formula I)

wherein $R^1$ and $R^2$ which may be the same or different represent hydrogen, chloro or —$(CH_2CH_2)$—$R^3$ (wherein $R^3$ is Ph, $CH_2Cl$, $C_nH_{2n}CH_3$ (n=0–15), $CF_3$, $CH_2CF_3$, Si(Me)$_m$Cl$_{3-m}$(m=0–3), CN, $CH_2CN$, (p—Ph)—$CH_2Cl$ or 3-cyclohexenyl group); Ar represents phenyl ring, phenoxyphenyl ring, or biphenyl ring; $X^1$ represents hydrogen or methyl; and $X^2$ represents hydrogen, alkyl($C_1$–$C_4$), fluoro, chloro, bromo, phenyl or phenoxy group.

2. A method to prepare bis(silylpropyl)arenes represented by the formula I by reacting aromatic compounds represented by the formula II or III with allylchlorosilanes represented by the formula IV in the presence of a Lewis acid catalyst;

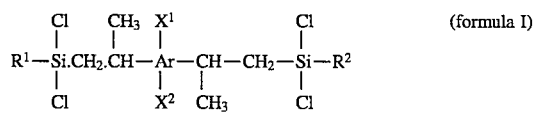
(formula I)

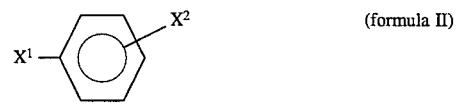
(formula II)

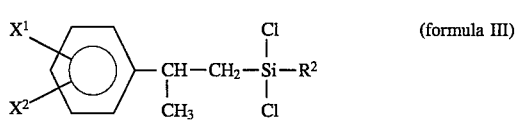
(formula III)

-continued $$\begin{array}{c} Cl \\ | \\ H_2C=CH-CH_2-Si-R^1 \\ | \\ Cl \end{array}$$ (formula IV)

wherein $R^1$ and $R^2$ which may be the same or different represent hydrogen, chloro or —$(CH_2CH_2)$—$R^3$ (wherein $R^3$ is Ph, $CH_2Cl$, $C_nH_{2n}CH_3$ (n=0–15), $CF_3$, $CH_2CF_3$, Si(Me)$_m$Cl$_{3-m}$(m=0–3), CN, $CH_2CN$, (p—Ph)—$CH_2Cl$ or 3-cyclohexenyl group); Ar represents phenyl ring, phenoxyphenyl ring, or biphenyl ring; $X^1$ represents hydrogen or methyl; and $X^2$ represents hydrogen, alkyl($C_1$–$C_4$), fluoro, chloro, bromo, phenyl or phenoxy group.

3. The method according to claim 2 wherein the Lewis acid catalyst is aluminum chloride.

4. The method for preparation of symmmetric bis(silylpropyl)arenes according to claim 3 which comprises reacting one mole of aromatic compounds represented by the formula II with two moles of allylchlorosilanes represented by the formula IV in the presence of aluminum chloride catalyst.

5. The method for preparation of symmmetric bis(silylpropyl)arenes according to claim 3 which comprises reacting one mole of silyl substituted aromatic compounds represented by the formula III with one mole of allylchlorosilanes represented by the formula IV wherein $R^2$ of the compound of formula III and $R^1$ of the compound of formula IV are the same, in the presence of aluminum chloride catalyst.

6. The method for preparation of asymmmetric bis(silylpropyl)arenes according to claim 3 which comprises reacting one mole of silyl substituted aromatic compounds represented by the formula III with one mole of allylchlorosilanes represented by the formula IV wherein $R^2$ of the compound of formula III and $R^1$ of the compound of formula IV are different from each other, in the presence of aluminum chloride catalyst.

7. The method according to claim 6 wherein $R^1$ is —$(CH_2CH_2)$—$R^3$ (wherein $R^3$ is Ph, $CH_2Cl$, $C_nH_{2n}CH_3$ (n=0–15), $CF_3$, $CH_2CF_3$, $Si(Me)_mCl_{3-m}$(m=0–3), CN, $CH_2CN$, (p—Ph)—$CH_2Cl$ or 3-cyclohexenyl group) and $R^2$ is hydrogen or chloro group.

8. The method according to claim 6 wherein $R^1$ is hydrogen or chloro group and $R^2$ is —$(CH_2CH_2)$—$R^3$ (wherein $R^3$ is Ph, $CH_2Cl$, $C_nH_{2n}CH_3$ (n=0–15), $CF_3$, $CH_2CF_3$, $Si(Me)_mCl_{3-m}$(m=0–3), CN, $CH_2CN$, (p—Ph)—$CH_2Cl$ or 3-cyclohexenyl group).

9. The method according to claim 4, wherein the amount of the aluminum chloride catalyst is 1–20 wt % of the aromatic compounds of formula II or III.

10. The method according to claim 5, wherein the amount of aluminum chloride catalyst is 1–20% of aromatic compounds of formula II or III.

11. The method according to claim 6, wherein the amount of the aluminum chloride catalyst is 1–20% of the aromatic compounds of formula II or III.

12. The method accordng to claim 7, wherein the amount of the aluminum chloride catalyst is 1–20% of the aromatic compounds of formula II or III.

13. The method according to claim 8, wherein the amount of the aluminum chloride catalyst is 1–20% of the aromatic compounds of formula II or III.

* * * * *